(12) United States Patent
Kuronuma et al.

(10) Patent No.: US 10,973,459 B2
(45) Date of Patent: Apr. 13, 2021

(54) HEAD-MOUNTED APPARATUS

(71) Applicant: Sony Interactive Entertainment Inc., Tokyo (JP)

(72) Inventors: Toru Kuronuma, Tokyo (JP); Toshihiro Kusunoki, Tokyo (JP); Hirohito Suzuki, Tokyo (JP)

(73) Assignee: SONY INTERACTIVE ENTERTAINMENT INC., Tokyo (JP)

( * ) Notice: Subject to any disclaimer, the term of this patent is extended or adjusted under 35 U.S.C. 154(b) by 226 days.

(21) Appl. No.: 16/127,594

(22) Filed: Sep. 11, 2018

(65) Prior Publication Data
US 2019/0090808 A1  Mar. 28, 2019

(30) Foreign Application Priority Data

Sep. 26, 2017  (JP) .............. JP2017-184645

(51) Int. Cl.
*A61B 5/00* (2006.01)
*A61B 5/0205* (2006.01)
*A61B 5/026* (2006.01)
*A61B 5/0476* (2006.01)
*G02B 27/01* (2006.01)
*G06F 3/01* (2006.01)
*G09G 3/20* (2006.01)
*G09G 3/00* (2006.01)

(52) U.S. Cl.
CPC .......... *A61B 5/6803* (2013.01); *A61B 5/0205* (2013.01); *A61B 5/0261* (2013.01); *A61B 5/0476* (2013.01); *A61B 5/6831* (2013.01); *A61B 5/6843* (2013.01); *G02B 27/0176* (2013.01); *A61B 2560/0462* (2013.01); *A61B 2560/0468* (2013.01); *A61B 2562/063* (2013.01); *G06F 3/015* (2013.01); *G09G 3/003* (2013.01); *G09G 3/2096* (2013.01); *G09G 2380/08* (2013.01)

(58) Field of Classification Search
CPC ... A61B 5/6803; A61B 5/0205; A61B 5/0261; A61B 5/0476; A61B 5/6831; A61B 5/6843; A61B 2560/0462; A61B 2560/0468; G09G 3/003; G09G 3/2096; G02B 27/0176
USPC ........................................................ 600/301
See application file for complete search history.

(56) References Cited

U.S. PATENT DOCUMENTS

2014/0276014 A1* 9/2014 Khanicheh ......... A61B 5/14553
600/425

FOREIGN PATENT DOCUMENTS

WO  WO 2015/137165 A1  9/2015

\* cited by examiner

*Primary Examiner* — Mallika D Fairchild
*Assistant Examiner* — Minh Duc G Pham
(74) *Attorney, Agent, or Firm* — Katten Muchin Rosenman LLP

(57) ABSTRACT

Disclosed herein is a head-mounted apparatus, including: an optical sensor having a contact face for contacting with the head of a user; a supporting unit disposed around the optical sensor and configured to contact with the head of the user; and a sensor supporting mechanism configured to support the optical sensor so as to permit a movement of the optical sensor in a contact direction that is a direction perpendicular to the contact face.

11 Claims, 4 Drawing Sheets

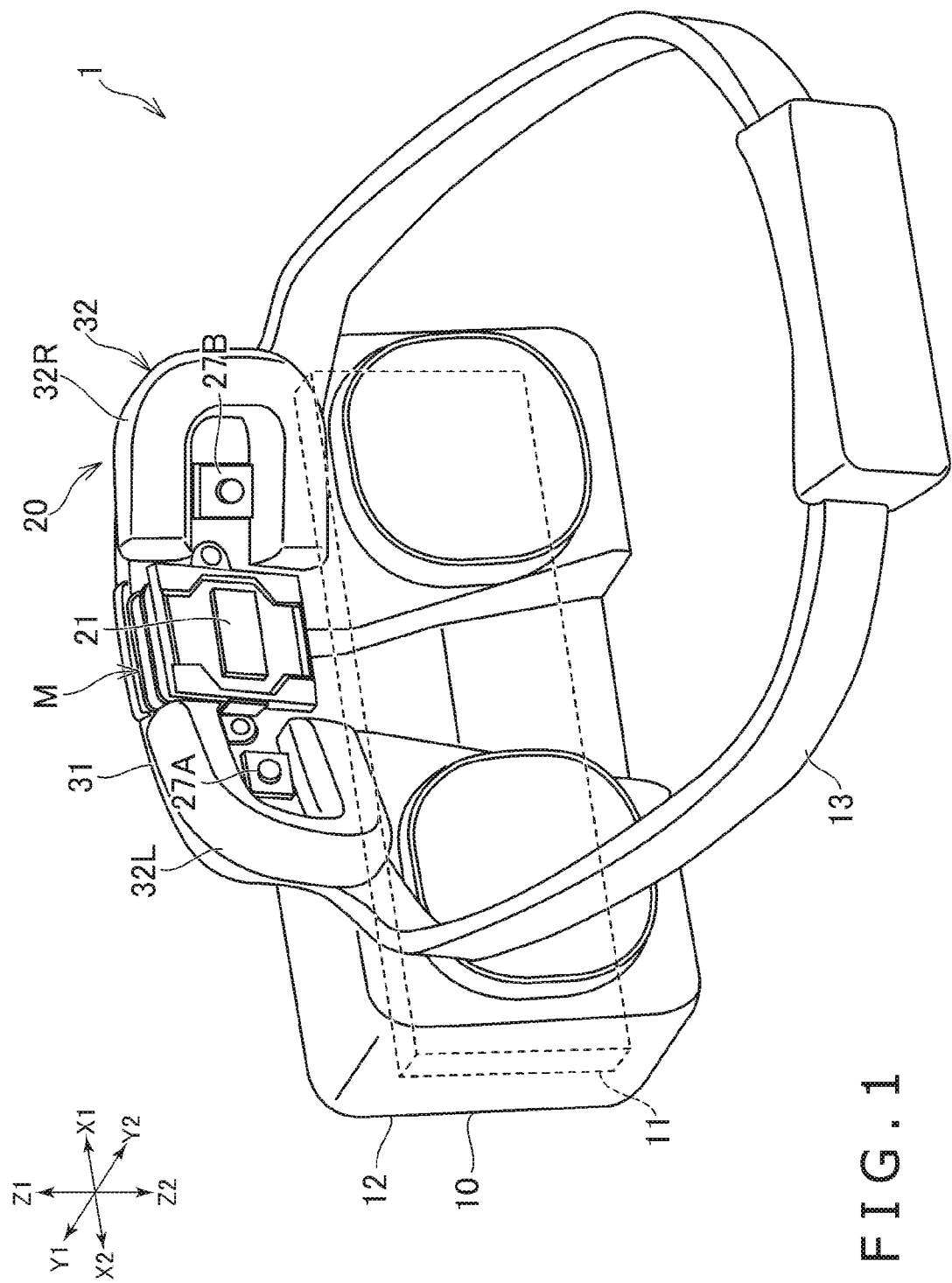
F I G. 1

HEAD-MOUNTED APPARATUS

BACKGROUND

The technology discussed herein relates to a head-mounted apparatus.

In related art, development of an apparatus for detecting biological information such as an electroencephalogram or a blood flow amount has been and is being underway. Japanese Patent Laid-Open No. 2013-146371 discloses a sensor that uses light to detect a blood flow. Some of such sensors for detecting biological information are used in a state in which they contact closely with the skin of a subject.

Further, a head-mounted apparatus that is mounted on the head of a user is known. For example, PCT Patent Publication No. WO2015/137165 discloses a head-mounted display for appreciating a video or for a like purpose. The head-mounted display receives video data generated by a video generation apparatus such as a game apparatus or an audio-visual apparatus and displays the received video data on a display apparatus disposed in front of the user's eyes.

SUMMARY

It is being studied to incorporate a sensor for detecting biological information into a head-mounted apparatus. If it is tried to stably mount a head-mounted apparatus on the head of a user, then some degree of force works between the head-mounted apparatus and the head. If this increases the contact pressure between the sensor and the skin, then the detection accuracy of biological information sometimes degrades. For example, in the case where the blood flow amount is to be detected as biological information, the high contact pressure influences on the blood flow, resulting in a problem that the detection accuracy of the blood flow amount degrades.

The head-mounted apparatus proposed herein includes an optical sensor having a contact face for contacting with the head of a user, a supporting unit disposed around the optical sensor and configured to contact with the head of the user, and a sensor supporting mechanism configured to support the optical sensor so as to permit a movement of the optical sensor in a contact direction that is a direction perpendicular to the contact face. With the head-mounted apparatus, the contact face of the optical sensor can be closely contacted with a moderate contact pressure with the head of a user, and the detection accuracy of biological information can be improved.

BRIEF DESCRIPTION OF THE DRAWINGS

FIG. 1 is a perspective view depicting a head-mounted display that is an example of an embodiment of the present disclosure;

DETAILED DESCRIPTION OF THE PREFERRED EMBODIMENT

In the following, an embodiment of the present disclosure is described. In the present specification, a head-mounted display as an example of the embodiment of the present disclosure is described. The present disclosure may be applied to an apparatus that is different from the head-mounted display, for example, a head-mounted apparatus that does not include a display and detects a brain movement.

Figure 2:
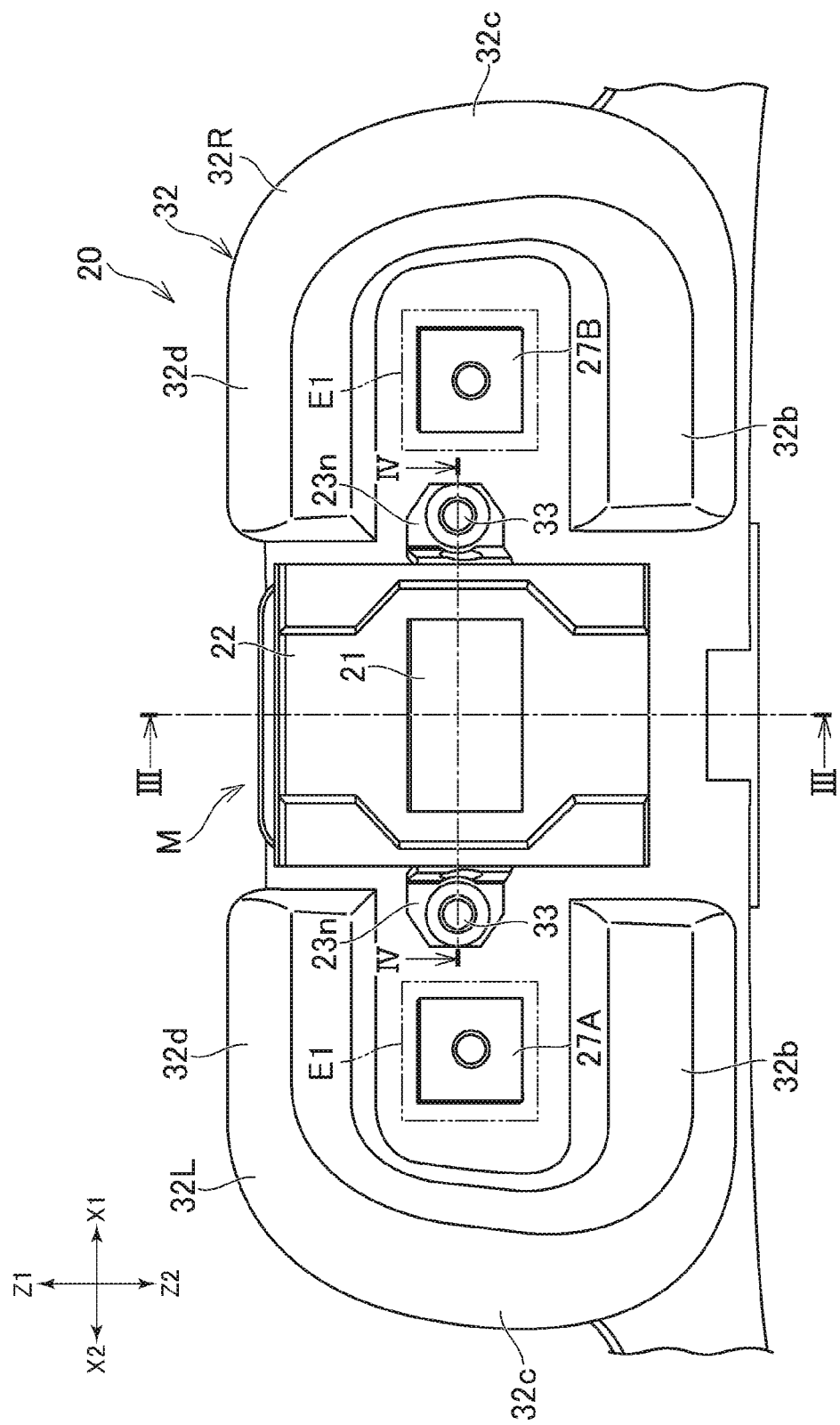
FIG. 2 is a rear elevational view of a portion of the head-mounted display at which a blood flow sensor is disposed.

In the following description, the directions indicated by arrow marks Y1 and Y2 of FIG. 1 are referred to as forward direction and rearward direction, respectively, and the directions indicated by arrow marks Z1 and Z2 of FIG. 1 are denoted as upward direction and downward direction, respectively. Further, the directions indicated by arrow marks X1 and X2 of FIG. 2 are denoted as rightward direction and leftward direction, respectively. Further, in the following direction, the head-mounted display is referred to as HMD.

As depicted in FIG. 1, the HMD 1 includes an apparatus main body 10 that has a display apparatus 11 built therein. Although the display apparatus 11 is, for example, a liquid crystal display apparatus or an organic electroluminescence display apparatus, the kind of it is not restricted specifically. When the HMD 1 is used, the apparatus main body 10 covers the front of the eyes of the user. The apparatus main body 10 includes a housing 12 in which the display apparatus 11 is accommodated.

As depicted in FIG. 1, the HMD 1 has a mounting unit 20 at a front portion thereof. In the mounting unit 20, a blood flow sensor 21 hereinafter described for detecting the blood flow amount of the forehead of the user and electroencephalogram sensors 27A and 27B for detecting an electroencephalogram are provided. The mounting unit 20 is positioned on the upper side of the apparatus main body 10 and is connected to the apparatus main body 10. When the HMD 1 is used, the mounting unit 20 is applied to the forehead of the user. The mounting unit 20 (more particularly, a frame 31 of the mounting unit 20) is curved so as to conform to the shape of the forehead of a person.

As depicted in FIG. 1, the HMD 1 has a mounting belt 13 that is to be wrapped around the head of the user. In the example of the HMD 1, the mounting belt 13 is connected to the right side and the left side of the mounting unit 20. Further, the mounting belt 13 and the mounting unit 20 have an annular shape surrounding the head as viewed in plan. The mounting belt 13 may be configured such that it has an adjustable length. The attachment position of the mounting belt 13 is not limited to the example of the HMD 1. For example, the mounting belt 13 may otherwise be connected not to the mounting unit 20 but to the apparatus main body 10.

Figure 3:
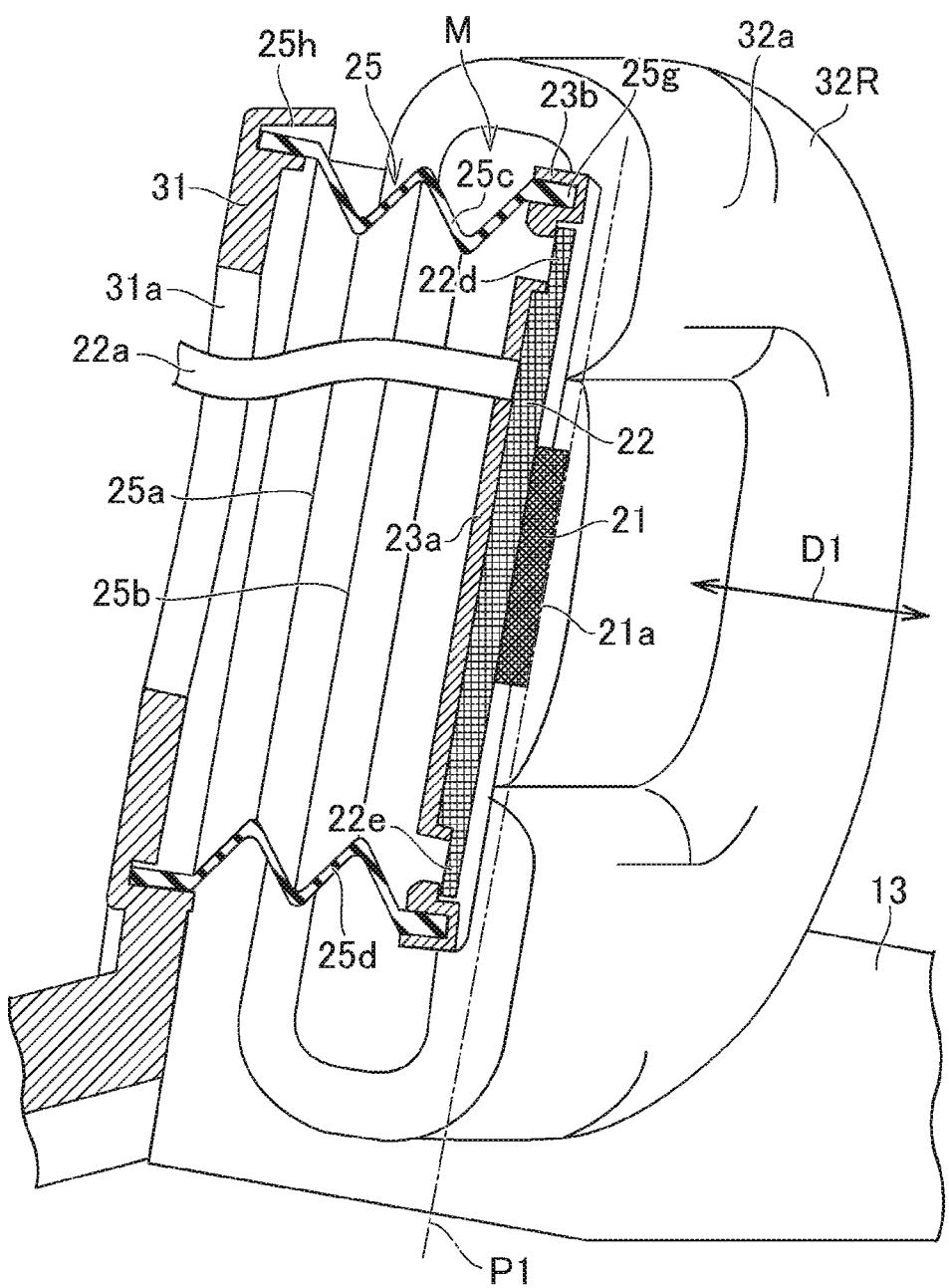
FIG. 3 is a cross sectional view taken along line III-III of FIG. 2.

As depicted in FIG. 3, the mounting unit 20 includes a blood flow sensor 21 and a sensor supporting mechanism M for supporting the blood flow sensor 21. Further, the mounting unit 20 has a supporting unit 32 disposed around the blood flow sensor 21 and a frame 31 (in the following description, the frame 31 is referred to as "front side frame").

The blood flow sensor 21 is an optical sensor that measures the blood flow amount. The blood flow sensor 21 irradiates light (for example, a laser beam) upon the forehead and measures the cerebral blood flow from reflected light of the same. The blood flow sensor 21 includes a light emitting element (for example, a laser diode) and a light receiving element (for example, a photodiode). Thus, the blood flow sensor 21 irradiates, for example, infrared rays on the forehead and detects the scattered light by the light receiving element. The blood flow sensor 21 measures a variation of the blood flow amount in the proximity of the surface of the cerebrum from the light detected by the light receiving element. The blood flow sensor 21 may have a plurality of light receiving elements. Further, the blood flow sensor 21 may have a plurality of light emitting elements.

The HMD 1 is connected by wireless connection or wired connection to a video generation apparatus such as, for example, a game apparatus, an audio-visual apparatus or a personal computer. Thus, the HMD 1 receives video data from the video generation apparatus and displays the video data on the display apparatus 11. Further, the HMD 1 transmits information of the blood flow amount detected by the blood flow sensor 21 to the video generation apparatus. The video generation apparatus reflects the information of the blood flow amount received from the HMD 1 on the video data to be generated by the video generation apparatus. In other words, the video generation apparatus generates (including correction) video data to be transmitted to the HMD 1 on the basis of the data of the blood flow amount received from the HMD 1.

As depicted in FIG. 2, in the example of the HMD 1, the blood flow sensor 21 is disposed at a central location of the mounting unit 20 in the leftward and rightward direction. As hereinafter described, the sensor supporting mechanism M supports the blood flow sensor 21 so as to permit a variation of the position and the posture of the blood flow sensor 21. The disposition of the blood flow sensor 21 is not limited to that of the example of the HMD 1. For example, the position of the blood flow sensor 21 may be displaced in the rightward direction or the leftward direction from the center of the mounting unit 20 in the leftward and rightward direction. The HMD 1 may have a plurality of blood flow sensors 21. In this case, the plurality of blood flow sensors 21 may be lined up in the leftward and rightward direction or in the upward and downward direction.

The front side frame 31 has, for example, a form of a plate. As depicted in FIG. 1, parts configuring the mounting unit 20 such as the supporting unit 32 and the sensor supporting mechanism M are attached to the front side frame 31. The mounting belt 13 described hereinabove is connected, for example, to the front side frame 31. The front side frame 31 is curved so as to conform to the shape of the forehead of a person. The front side frame 31 is formed, for example, from plastics. The front side frame 31 may be one member formed integrally or may be configured from a plurality of members individually formed integrally. For example, a portion (first portion) to which the sensor supporting mechanism M is attached and another portion (second portion) to which the supporting unit 32 is attached may be formed separately from each other, and the first portion may be attached to the second portion.

As depicted in FIG. 1, the supporting unit 32 is attached to a rear face of the front side frame 31. The surface (rear face) 32a of the supporting unit 32 (refer to FIG. 3) contacts with the forehead of the user when the HMD 1 is used. Therefore, the supporting unit 32 can function as a spacer for assuring a distance between the front side frame 31 and the forehead of the user. Since the supporting unit 32 contacts with the forehead of the user, the blood flow sensor 21 can be prevented from being pressed strongly against the forehead of the user. For example, in the case where the mounting unit 20 is pressed against the forehead of the user because the length of the mounting belt 13 is decreased by the user, the pressing force acts upon the supporting unit 32 while high force does not act upon the blood flow sensor 21. The supporting unit 32 has elasticity for urging the surface 32a of the supporting unit 32 toward the forehead of the user. In other words, the supporting unit 32 is formed from a maternal having a cushioning property. The supporting unit 32 can be formed, for example, from rubber or a foamed material.

As depicted in FIG. 2, in the example of the HMD 1, the supporting unit 32 has two portions 32R and 32L positioned on the opposite sides to each other across the blood flow sensor 21 (in other words, across the sensor supporting mechanism M) (in the following description, each of the portions 32R and 32L is referred to as "half"). In the example of the HMD 1, the supporting unit 32 has a right half 32R disposed on the right side with respect to the blood flow sensor 21 and a left half 32L disposed on the left side with respect to the blood flow sensor 21. The halves 32R and 32L have, for example, a substantially U shape open toward the blood flow sensor 21. In particular, each of the halves 32R and 32L has an upper horizontal portion 32d extending in the leftward and rightward direction at an upper portion of the mounting unit 20, a lower horizontal portion 32b extending in the leftward and rightward direction at a lower portion of the mounting unit 20, and a vertical portion 32c that connects the upper horizontal portion 32d and the lower horizontal portion 32b to each other. Other parts such as, for example, electroencephalogram sensors 27A and 27B hereinafter described, a circuit board and a battery may be disposed in a region E1 on the inner side of each of the halves 32R and 32L.

The shape or disposition of the supporting unit 32 is not limited to that of the example of the HMD 1. For example, the supporting unit 32 may include a portion positioned on the upper side with respect to the blood flow sensor 21 and/or a portion positioned on the lower side with respect to the blood flow sensor 21. In another example, the supporting unit 32 may have a quadrangular shape or a circular shape. In this case, the supporting unit 32 may include or may not include the regions E1 in which other parts are disposed. In a further example, the halves 32R and 32L may each include the vertical portion 32c that connects the upper horizontal portion 32d and the lower horizontal portion 32b.

The blood flow sensor 21 has a contact face 21a (refer to FIG. 3) for contacting with the forehead of the user. A light emitting element and a light receiving element are provided on the contact face 21a. If a gap exists between the contact face 21a and the skin of the forehead, then external light enters the gap and the blood flow amount cannot be detected appropriately. Therefore, it is necessary for the contact face 21a to closely contact with the skin. However, if the contact pressure between the contact face 21a and the skin is high, then the high contact pressure influences on the blood flow amount, resulting in degradation of the detection accuracy of the blood flow amount. Therefore, it is necessary for the contact face 21a to closely contact with the skin with an appropriate contact pressure (comparatively low contact pressure).

Therefore, in the example of the HMD 1, the supporting unit 32 is disposed around the blood flow sensor 21. Further, the sensor supporting mechanism M supports the blood flow sensor 21 so as to permit a movement of the blood flow sensor 21 in a direction (Dl direction in FIG. 3) perpendicular to the contact face 21a (in the following description, the Dl direction is referred to as "contact direction." In the present specification, the "contact direction" is a direction orthogonal to the contact face 21a when the blood flow sensor 21 is at its initial position). According to this structure, the contact face 21a can closely contact with the skin with an appropriate contact pressure.

As depicted in FIG. 3, the sensor supporting mechanism M has an expansion and contraction unit 25 that is expandable and contractible in the contact direction and supports the blood flow sensor 21 through the expansion and contraction unit 25. In particular, the sensor supporting mechanism M supports the blood flow sensor 21 in a floating manner in the contact direction, and the expansion and contraction unit 25 functions as a floating spring. The expansion and contraction unit 25 includes, for example, bellows. In particular, the expansion and contraction unit 25 has a plurality of folds 25a and 25b such that the valley folds 25a and the mountain folds 25b are lined up alternately in the contact direction. If bellows are used as the expansion and contraction unit 25 in this manner, then the variation of the contact pressure caused by displacement of the blood flow sensor 21 can be reduced in comparison with that in an alternative case in which, for example, a spring is used as the expansion and contraction unit 25. Therefore, even in the case where the tightening of the mounting belt 13 is increased, the contact pressure can be kept fixed.

The expansion and contraction unit 25 is formed from rubber (for example, silicone rubber, urethane rubber, acrylic rubber or the like). Further, the expansion and contraction unit 25 has a shape of a tube extending in the contact direction and is hollow in the inside thereof. In particular, the expansion and contraction unit 25 has an upper face portion 25c (refer to FIG. 3), a lower face portion 25d (refer to FIG. 3), a right side face portion 25e (refer to FIG. 4) and a left side face portion 25f (refer to FIG. 4), and a space is formed in the inner side of them.

The expansion and contraction unit 25 has elasticity for urging the blood flow sensor 21 toward the forehead of the user. Consequently, the contact face 21a can closely contact with the forehead of the user. Preferably, the expansion and contraction unit 25 has a low elastic modulus. If the expansion and contraction unit 25 has a low elastic modulus, then the load (contact pressure) acting from the blood flow sensor 21 upon the forehead of the user can be suppressed from being changed by the shape of the forehead of the user or by the degree of tightening of the mounting belt 13 (in other words, the length of the mounting belt 13). For example, even in the case where the supporting unit 32 is pressed against the forehead of the user with comparatively strong force because the mounting belt 13 is shortened, the blood flow sensor 21 can contact with the forehead of the user with moderate force. The expansion and contraction unit 25 has an elastic modulus, for example, lower than that of the supporting unit 32.

It is to be noted that the expansion and contraction unit 25 may not be bellows. For example, the expansion and contraction unit 25 may have only one fold in place of the plurality of folds 25a and 25b lined up alternately in the contact direction. Further, the sensor supporting mechanism M may have one or a plurality of springs as the expansion and contraction unit 25. In this case, preferably a spring having a comparatively low elastic modulus is used as the expansion and contraction unit 25.

Preferably, the blood flow sensor 21 is designed such that it contacts with the forehead irrespective of the shape of the forehead of the user. In particular, the blood flow sensor 21 is disposed such that the contact face 21a thereof is positioned, for example, on the forehead side of the user with respect to an imaginary curved plane formed from the surface (rear face) 32a of the supporting unit 32. In other words, the contact face 21a of the blood flow sensor 21 is positioned rearwardly with respect to the curved plane formed from the surface 32a of the supporting unit 32.

As depicted in FIG. 3, the blood flow sensor 21 is mounted on a board 22 (in the following description, the board 22 is referred to as "sensor board"). A driving circuit for the blood flow sensor 21 may be mounted on the sensor board 22. Further, to the sensor board 22, an electrical wire 22a that connects the driving circuit for the blood flow sensor 21 and a different circuit or part the HMD 1 has to each other may be connected. In the example of the HMD 1, the sensor board 22 passes the inner side of the tubular expansion and contraction unit 25 and extends forwardly. The sensor supporting mechanism M has a sensor frame 23 to which the sensor board 22 is attached. The sensor board 22 is attached to a central portion 23a of the sensor frame 23.

As depicted in FIG. 3, the sensor frame 23 has an outer peripheral portion 23b to which a rear edge 25g of the tubular expansion and contraction unit 25 is connected. As described hereinabove, the tubular expansion and contraction unit 25 has a tubular shape having the upper face portion 25c, lower face portion 25d, right side face portion 25e and left side face portion 25f. The outer peripheral portion 23b has a rectangular shape, and the upper face portion 25c, lower face portion 25d, right side face portion 25e and left side face portion 25f are connected at the rear edge 25g thereof to the outer peripheral portion 23b. By the configuration, the sensor frame 23 and the sensor board 22 can move together with each other in the contact direction.

As depicted in FIG. 3, a front edge 25h of the expansion and contraction unit 25 is connected to the front side frame 31. The front side frame 31 has an opening 31a formed therein so as to be positioned in front of the expansion and contraction unit 25. The inside space of the expansion and contraction unit 25 is communicated with the outside through the opening 31a. When the expansion and contraction unit 25 expands or contracts, the air can go into and out of the inside of the expansion and contraction unit 25 through the opening 31a. As a result, the expansion and contraction unit 25 can expand and contract smoothly. The electrical wire 22a connected to the sensor board 22 extends through the opening 31a of the front side frame 31.

The sensor supporting mechanism M supports the blood flow sensor 21 such that it permits tilting of the contact face 21a of the blood flow sensor 21. Here, the "tilting of the contact face 21a" is tilting of the contact face 21a with respect to a plane P1 depicted in FIGS. 3 and 4. The plane P1 is a plane parallel to the contact face 21a when the blood flow sensor 21 is at its initial position (position of the blood flow sensor 21 depicted in FIGS. 3 and 4). According to this structure, the posture of the blood flow sensor 21 can be changed in conformity with the shape of the forehead of the user. As a result, the close contact property between the contact face 21a and the forehead of the user can be improved.

Figure 4:
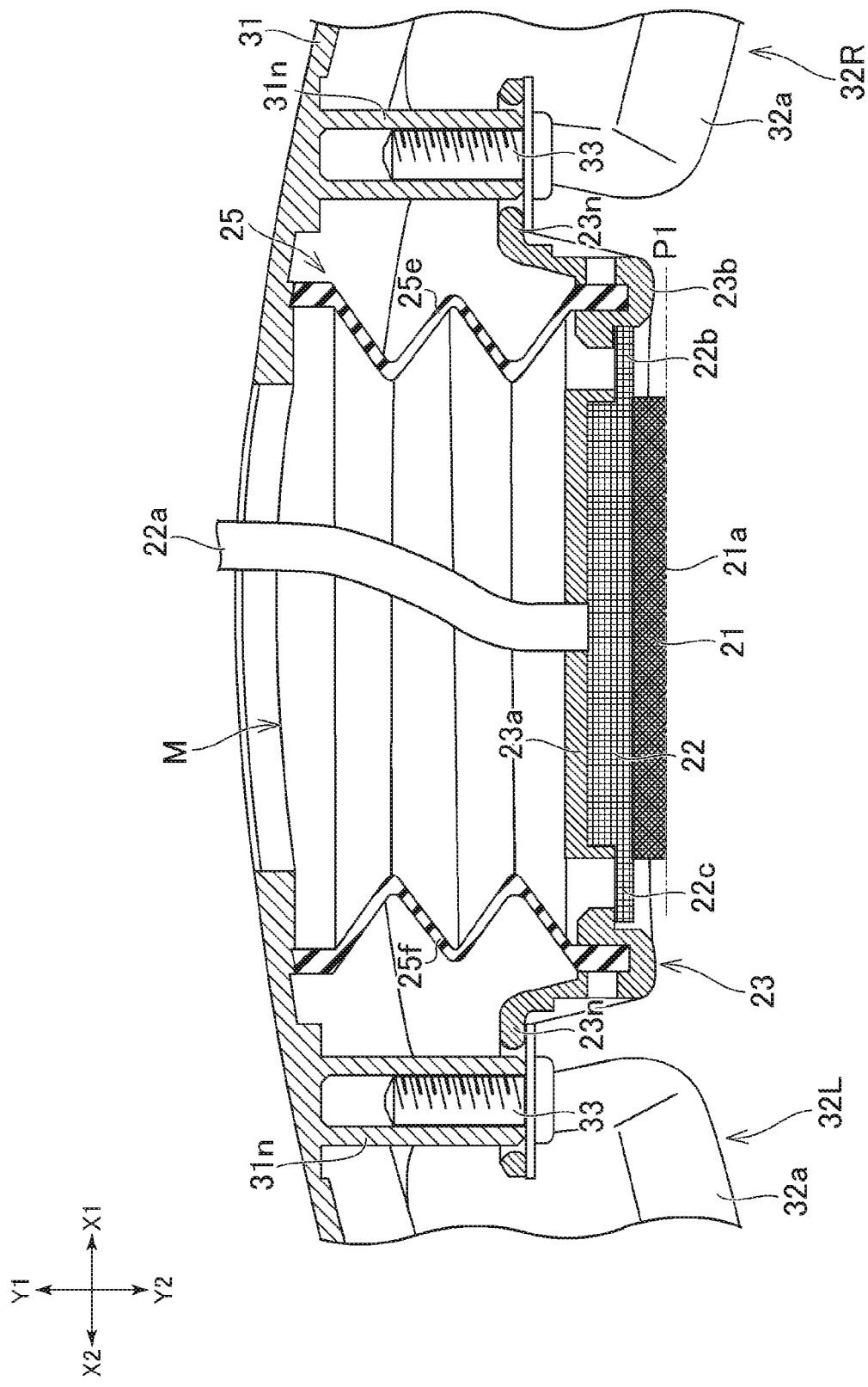
FIG. 4 is a cross sectional view taken along line IV-IV of FIG. 2.

The front side frame 31 has a guide portion 31n for guiding the sensor frame 23 such that the sensor frame 23 can move in the contact direction. In the example of the HMD 1, the front side frame 31 has guide portions 31n at two locations positioned on the opposite sides to each other across the sensor supporting mechanism M. As depicted in FIG. 4, the guide portions 31n are provided on the right side and the left side with respect to the sensor supporting mechanism M. The guide portions 31n extend in the contact direction from the front side frame 31. More particularly, the guide portions 31n are bosses projecting from the front side frame 31. Meanwhile, the sensor frame 23 has two guided portions 23n individually movable along the two guide portions 31n. In the example of the HMD 1, the guided portions 23n are formed on a right edge and a left edge of the outer peripheral portion 23b of the sensor frame 23.

As depicted in FIG. 4, an opening is formed in each of the guided portions 23n. The guide portions 31n are fitted in the openings. Consequently, the sensor frame 23 is supported by the guide portions 31n. In particular, the movement of the sensor frame 23 with respect to the guide portions 31n in the upward and downward direction and the leftward and rightward direction is restricted. Further, the guided portions 23n are movable in the contact direction along the guide portions 31n. Each of the guide portions 31n has at an end portion thereof a stopper member 33 for restricting the guided portion 23n from the guide portion 31n so as not to be pulled off. For example, a screw can be used as the stopper member 33. As described hereinabove, the expansion and contraction unit 25 has elasticity and urges the blood flow sensor 21 in the contact direction (rearward direction). When the left and right guided portions 23n contact with the stopper members 33 of the left and right guide portions 31n, respectively, the blood flow sensor 21 is disposed at its initial position.

The two guided portions 23n formed on the sensor frame 23 can move separately from each other along the guide portions 31n. Accordingly, a right edge 22b (refer to FIG. 4) and a left edge 22c (refer to FIG. 4) of the sensor board 22 can move separately from each other in the contact direction. As a result, the contact face 21a of the blood flow sensor 21 can be tilted in the rightward direction or in the leftward direction.

The opening of each of the guided portions 23n has a diameter greater than that of the guide portions 31n, and each guided portion 23n can tilt with respect to the guide portion 31n. As a result, an upper edge 22d (refer to FIG. 3) and a lower edge 22e (refer to FIG. 3) of the sensor board 22 can move separately from each other in the contact direction. As a result, the contact face 21a of the blood flow sensor 21 can be tilted in the upward direction or in the downward direction.

It is to be noted that the supporting structure for the sensor board 22 is not necessarily limited to that of the example depicted in FIG. 4 only if tilting of the sensor board 22 is permitted. For example, the positions of the guide portions 31n formed on the front side frame 31 may be positions on the upper side and the lower side of the sensor supporting mechanism M. Further, in another example, the guide portions 31n and the guided portions 23n are formed on the inner side of the expansion and contraction unit 25. In a further example, the number of guide portions 31n is not limited to two but may be three or four.

As depicted in FIG. 2, the mounting unit 20 has the electroencephalogram sensors 27A and 27B. The electroencephalogram sensors 27A and 27B are, for example, electrodes and detect a variation of a potential difference generated between two points of the surface of the head of the user as an electroencephalogram. The HMD 1 transmits information of the electroencephalogram to a video generation apparatus such as a game apparatus. The video generation apparatus reflects the information of the electroencephalogram received from the HMD 1 on video data to be generated by the video generation apparatus. In other words, the video generation apparatus generates (corrects) video data to be transmitted to the HMD 1 on the basis of the information of the electroencephalogram received from the HMD 1.

In the example of the HMD 1, the electroencephalogram sensors 27A and 27B are disposed on the right side and the left side with respect to the blood flow sensor 21, respectively. When the HMD 1 is used, the electroencephalogram sensors 27A and 27B contact with the upper side with respect to the eyebrows of the user. By disposing the electroencephalogram sensors 27A and 27B at the positions just described, when the HMD 1 is used, the electroencephalogram sensors 27A and 27B are permitted to be pressed sufficiently against the forehead of the user. As a result, the detection accuracy of the electroencephalogram can be improved. It is to be noted that, when the HMD 1 is used, the contact pressure between the blood flow sensor 21 and the forehead of the user is lower than the contact pressure between the electroencephalogram sensors 27A and 27B and the forehead of the user.

As described hereinabove, each of the left and right halves 32R and 32L the supporting unit 32 has a region E1 on the inner side thereof. In the example of the HMD 1, the electroencephalogram sensors 27A and 27B are disposed in the regions E1 and are surrounded by the halves 32R and 32L, respectively. In this manner, in the example of the HMD 1, the regions E1 on the inner side of the supporting unit 32 are utilized effectively to dispose the electroencephalogram sensors 27A and 27B, and the size of the mounting unit 20 can be reduced thereby.

The disposition of the electroencephalogram sensors 27A and 27B is not limited to that of the example of the HMD 1 but may be changed suitably. For example, the electroencephalogram sensors 27A and 27B may be disposed on the upper side with respect to the sensor supporting mechanism M or may be disposed on the lower side with respect to the sensor supporting mechanism M. Further, while, in the example of FIG. 2, the mounting unit 20 has the two electroencephalogram sensors 27A and 27B, the number of the electroencephalogram sensors 27A and 27B may be greater than 2.

As described above, the HMD 1 includes a blood flow sensor 21 having a contact face 21a for contacting with the head of a user, a supporting unit 32 disposed around the blood flow sensor 21 and configured to contact with the head of the user, and a sensor supporting mechanism M that supports the blood flow sensor 21 so as to permit a movement of the blood flow sensor 21 in a contact direction that is a direction perpendicular to the contact face 21a. With the apparatus just described, the contact face 21a can closely contact with the forehead of the user with a moderate contact pressure, and the detection accuracy of the blood flow amount can be improved.

It is to be noted that the present disclosure is not limited to the HMD 1 described above but may be changed suitably. For example, the present disclosure may be applied to a head-mounted apparatus that does not include the display apparatus 11 although it includes the blood flow sensor 21. As another example, the head-mounted apparatus may include a sensor configured to use light to detect biological information other than the blood flow amount and supported by the sensor supporting mechanism M.

The present disclosure contains subject matter related to that disclosed in Japanese Priority Patent Application JP 2017-184645 filed in the Japan Patent Office on Sep. 26, 2017, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A head-mounted apparatus, comprising:
an optical sensor having a rigid contact face for contacting with the head of a user;

an expansion and contraction unit surrounding the optical sensor and configured to contact with the head of the user, wherein the expansion and contraction unit includes bellows; and a supporting unit comprising a first supporting unit and a second supporting unit;

wherein the first supporting unit is arranged on a first side of the expansion and contraction unit, and wherein the second supporting unit is arranged on a second side of the expansion and contraction unit opposite the first side, wherein the expansion and contraction unit permits movement of the optical sensor in a floating manner in a contact direction that is a direction perpendicular to the rigid contact face, wherein the expansion and contraction unit moves independent of the supporting unit, and wherein the expansion and contraction unit has a lower elastic modulus than the supporting unit.

2. The head-mounted apparatus according to claim 1, wherein the expansion and contraction unit has elasticity that urges the rigid contact face toward the head, and wherein the supporting unit has elasticity that urges a face of the supporting unit toward the head.

3. The head-mounted apparatus according to claim 1, wherein the expansion and contraction unit supports the optical sensor so as to permit tilting of the rigid contact face.

4. The head-mounted apparatus according to claim 1, wherein the optical sensor is attached to a rigid sensor board; and the expansion and contraction unit supports the rigid sensor board such that a right edge and a left edge of the rigid sensor board can move separately from each other in the contact direction.

5. The head-mounted apparatus according to claim 1, wherein the optical sensor is attached to a rigid sensor board; and the expansion and contraction unit supports the rigid sensor board such that an upper edge and a lower edge of the rigid sensor board can move separately from each other in the contact direction.

6. The head-mounted apparatus according to claim 1, further comprising:

an electroencephalogram sensor surrounded on three sides by the first supporting unit on the first side of the expansion and contraction unit.

7. The head-mounted apparatus according to claim 6, wherein the optical sensor and the electroencephalogram sensor contact a forehead of the user.

8. The head-mounted apparatus according to claim 1, further comprising:

a first electroencephalogram sensor surrounded on three sides by the first supporting unit on the first side of the expansion and contraction unit, and a second electroencephalogram sensor surrounded on three sides by the second supporting unit on the second side of the expansion and contraction unit.

9. The head-mounted apparatus according to claim 1, wherein the optical sensor is a blood flow sensor.

10. The head-mounted apparatus according to claim 1, wherein the expansion and contraction unit and the supporting unit are coupled to a top of a main housing of the head-mounted apparatus above a display of the head-mounted apparatus.

11. The head-mounted apparatus according to claim 1, further comprising:

a mounting belt for coupling the head-mounted apparatus to the head of the user.

* * * * *